US009347888B2

(12) United States Patent
Ghirardi et al.

(10) Patent No.: US 9,347,888 B2
(45) Date of Patent: May 24, 2016

(54) DETECTION OF BACTERIA EXHIBITING A RESISTANCE TO CARBAPENEMS

(75) Inventors: Sandrine Ghirardi, Saint Genis les Ollières (FR); John Perry, Newcastle upon Tyne (GB); Gilles Zambardi, Chezeneuve (FR)

(73) Assignee: BIOMERIEUX, Marcy L'Etoile (FR)

( * ) Notice: Subject to any disclaimer, the term of this patent is extended or adjusted under 35 U.S.C. 154(b) by 0 days.

(21) Appl. No.: 14/001,565

(22) PCT Filed: Mar. 16, 2012

(86) PCT No.: PCT/FR2012/050556
§ 371 (c)(1),
(2), (4) Date: Aug. 26, 2013

(87) PCT Pub. No.: WO2012/131216
PCT Pub. Date: Oct. 4, 2012

(65) Prior Publication Data
US 2013/0344522 A1    Dec. 26, 2013

(30) Foreign Application Priority Data

Mar. 25, 2011    (FR) ...................................... 11 52477

(51) Int. Cl.
*G01N 21/76* (2006.01)
*C12N 1/20* (2006.01)
*C12N 15/01* (2006.01)
*C12Q 1/04* (2006.01)

(52) U.S. Cl.
CPC ................ *G01N 21/763* (2013.01); *C12N 1/20* (2013.01); *C12N 15/01* (2013.01); *C12Q 1/04* (2013.01)

(58) Field of Classification Search
None
See application file for complete search history.

(56) References Cited

FOREIGN PATENT DOCUMENTS

FR      2 925 070 A1       6/2009
WO   WO 2010/010083 A1    1/2010

OTHER PUBLICATIONS

Walsh, F., "Doripenem: A new carbapenem antibiotic a review of comparative antimicrobial and bactericidal activities", Therapeutics and Clinical Risk Management 2007:3(5) 789-794.*

Wexler et al., "In Vitro Activities of Faropenem against 579 Strains of Anaerobic Bacteria", Antimicrobial Agents and Chemotherapy, Nov. 2002, vol. 46, No. 11, pp. 3669-3675.*

Naiemi et al., "Extended-spectrum beta-lactamases screening agar with AmpC inhibition", Eur J Clin Microbiol Infect Dis (2009) 28:989-990. DOI 10.1007/s10096-009-0714-8.*

Rodel et al., "In vitro activities of faropenem, ertapenem, imipenem and meropenem against Borrelia burgdorferi s.l.", International Journal of Antimicrobial Agents 30 (2007) 83-86.*

Pages et al; "Efflux Pump, the Masked Side of β-Lactam Resistance in *Klebsiella pneumoniae* Clinical Isolates;" PLoS ONE; Mar. 2009; vol. 4; Issue 3; e4817.

Samra et al; "Evaluation of CHROMagar KPC for Rapid Detection of Carbapenem-Resistant *Enterobacteriaceae*;" Journal of Clinical Microbiology; Jul. 2008;vol. 46; No. 9; pp. 3110-3111.

Nordmann et al; "How to Detect NDM-1 Producers;" Journal of Clinical Microbiology; 2011; Dec. 2010; vol. 49; No. 2; pp. 718-721.

Mushtaq et al; "Activity of faropenem against cephalosporin-resistant Enterobacteriaceae;" Journal of Antimicrobial Chemotherapy; 2007; vol. 59; pp. 1025-1030.

Giske et al; "A sensitive and specific phenotypic assay for detection of metallo-β-lactamases and KPC in *Klebsiella pneumoniae* with the use of meropenem disks supplemented with aminophenylboronic acid, dipicolinic acid and cloxacillin;" Clinical Microbiology and Infection; Jun. 2010; vol. 17; No. 4; pp. 552-556.

Malléa et al; "Inhibitors of antibiotic efflux pump in resistant *Enterobacter aerogenes* strains;" Biochemical and Biophysical Research Communications; 2002; vol. 293; pp. 1370-1373.

Orenga et al; "Enzymatic substrates in microbiology;" Journal of Microbiological Methods; 2009; vol. 79; pp. 139-155.

Panagea et al; "Evaluation of CHROMagar™ KPC for the detection of carbapenemase-producing Enterobacteriaceae in rectal surveillance cultures;" International Journal of Antimicrobial Agents; 2010.

May 22, 2012 Search Report issued in International Patent Application No. PCT/FR2012/050556.

Translation of May 22, 2012 Written Opinion issued in International Patent Application No. PCT/FR2012/050556.

* cited by examiner

*Primary Examiner* — Suzanne M Noakes
(74) *Attorney, Agent, or Firm* — Oliff PLC

(57) ABSTRACT

Disclosed is a process for detecting and/or identifying, in a biological sample, bacteria exhibiting a resistance to carbapenems, including: a) contacting said sample with a reaction medium including at least one chromogenic agent and faropenem and/or doripenem; b) incubating the whole so as to allow the bacteria to grow; and c) detecting the strains exhibiting a resistance to carbapenems. The medium employed in step a) also contains cloxacillin and/or a combination of cloxacillin and PAbetaN.

21 Claims, No Drawings

DETECTION OF BACTERIA EXHIBITING A RESISTANCE TO CARBAPENEMS

The present invention relates to a detection and identification process suitable for screening bacteria which are resistant to carbapenems.

The increase in the resistance to beta-lactam antibiotics, such as penicillins and cephalosporins, complicates the treatment of infections caused by strains of Gram-negative bacteria. These antibiotics are then replaced by other broad-spectrum antimicrobials. Amongst these broad-spectrum antimicrobials, carbapenems have taken an important role, especially for treating hospitalised patients. Carbapenems act against the majority of Gram-positive and Gram-negative aerobic bacteria, and on certain anaerobic bacteria.

However, more and more strains resistant to carbapenems are appearing in hospitalised patients.

The bacteria concerned are, non-exhaustively, *Escherichia coli, Enterobacter cloacae, Enterobacter aerogenes, Citrobacter* sp., *Klebsiella pneumoniae, Klebsiella oxytoca, Pseudomonas aeruginosa, Providencia rettgeri, Pseudomonas putida, Stenotrophomonas maltophilia, Acinetobacter baumanii, Comamonas* sp., *Aeromonas* sp., *Morganella morganii, Enterococcus* sp., *Proteus mirabilis, Salmonella senftenberg, Serratia marcescens, Salmonella typhimurium*, etc.

The reduced susceptibility to carbapenems can be due to:
the expression of a gene which is resistant to beta-lactams:
  (i) hyperproduction of ampC beta-lactamases and/or
  (ii) ESBL (extended-spectrum beta-lactamase),
combined with changes in the permeability of the cell wall (impermeability resistance) and/or with the active efflux of the antibiotics (Pages et al., 2009; PloS ONE, 4 (3)); and/or
the existence of enzymes which break down carbapenems, called carbapenemases.

The carbapenemase genes may be present in chromosomes and/or in plasmids. Due to this presence in the form of plasmids, these kinds of enzymatic resistance are capable of spreading to a great extent and, consequently, pose a major risk in epidemiological terms.

The person skilled in the art has difficulty in easily detecting and/or identifying the strains of bacteria which are resistant to carbapenems.

A method of characterising by using a chromogenic medium comprising meropenem and/or ertapenem was suggested in Application WO 2010/010083 and implemented in the media CHROMagar® KPC (Samra et al., 2008; J. Clin. Microbiol., 46 (9): 3110-3111; CHROMagar™, Paris, France) and COLOREX™ KPC (BioMed Diagnostics Inc.). This medium does not permit the detection of all of the carbapenamase-producing strains, particularly the NDM-1 strains which have appeared recently (Nordmann et al., 2011; J Clin Microbiol., 49(2): 718-721). In the current epidemiological context, and particularly with the emergence of these new NDM-1 resistances, there is still a need to improve, in sensitivity and/or specificity, the screening of all of the mechanisms of resistance to carbapenems.

Faropenem and doripenem are recently developed and tested carbapenems (Mushtaq et al., 2007; Journal of Antimicrobial Chemotherapy, 59: 1025-1030—Lee et al., 2011, Microbial Drug Resistance). To the Applicant's knowledge, they have never been used to detect and/or identify, directly in biological samples, bacterial strains resistant to carbapenems.

The Applicant has shown that it is possible to improve the detection of strains resistant to carbapenems, more particularly all of the strains which produce carbapenemases, including KPC carbapenemases and NDM carbapenemases. This meets the demands linked to the current epidemiological context, in particular with the emergence of new resistances such as NDM-1, and permits the screening of all of the resistance mechanisms due to the production of all known types of carbapenemases.

In this respect, the present invention relates to a process for detecting and/or identifying, in a biological sample, bacteria exhibiting a resistance to carbapenems, comprising the steps consisting in:
  a) contacting said sample with a reaction medium comprising at least one chromogenic agent and faropenem and/or doripenem;
  b) incubating the whole so as to allow the bacteria to grow;
  c) detecting the strains exhibiting a resistance to carbapenems.

The Applicant has shown that the addition of faropenem and/or doripenem into a chromogenic medium makes it possible for the majority of carbapenemase-producing bacteria to grow, whilst inhibiting a majority of strains which do not produce them, such as wild strains, and strains which produce extended-spectrum beta-lactamases or high-level cephalosporinases, for example. The tests have made it possible to demonstrate a greater sensitivity and specificity than those of a chromogenic medium using meropenem.

According to a first embodiment, the present invention corresponds to a process for detecting and/or identifying, in a biological sample, bacteria exhibiting a resistance to carbapenems, comprising the steps consisting in:
  a) contacting said sample with a culture medium comprising at least one chromogenic substrate, and at least faropenem and/or doripenem;
  b) incubating the whole so as to allow the bacteria to grow;
  c) detecting the strains exhibiting a resistance to carbapenems.

According to a preferred embodiment of the invention, the bacteria are NDM-1 bacteria.

Preferably, the carbapenem concentrations are between 0.05 and 32 mg/L.

More preferably, the carbapenem concentrations are between 2 and 32 mg/L for faropenem, and between 0.05 and 2 mg/L for doripenem.

Advantageously, the medium employed in step a) also comprises cloxacillin and/or a combination of cloxacillin and PAbetaN. These compounds provide an additional level of selection and make it possible to distinguish the impermeability resistances and other non-enzymatic resistances from the resistances by production of carbapenemase.

Biological sample, is to be understood to be a small part or small isolated quantity of an entity for analysis. This can be a clinical sample, human or animal, from a specimen of biological liquid, or a food sample, from any type of food or a sample from the food production or processing environment. This sample can thus be liquid or solid. It is possible to cite in a non-limiting manner, a clinical sample of whole blood, serum, plasma, urines, faeces, specimens of nose, throat, skin, wounds, cerebrospinal fluid, a food sample of water, beverages such as milk, fruit juices, yoghurt, meat, eggs, vegetables, mayonnaise, cheese, fish, etc., a food sample from an animal feed, such as in particular an animal meal sample, or a sample for the control of a surface area or water body. This specimen can be used such as it is or, prior to the analysis, undergo preparation by enrichment, dilution, extraction, concentration or purification, in accordance with methods known to the person skilled in the art.

Reaction medium, is to be understood to be a medium comprising all the elements necessary for the expression of metabolism and/or for the growth of microorganisms. The reaction medium can be solid, semi-solid or liquid. Solid medium is understood to be a gelled medium, for example. Agar is the conventional gelling agent in microbiology for the culturing of microorganisms, but it is possible to use gelatine, agarose, or other natural or artificial gel-forming substances. A number of preparations are commercially available, for instance Columbia agar, Trypcase-soy agar, MacConkey agar or more generally those described in the Handbook of Microbiological Media (CRC Press).

The reaction medium may comprise one or more elements in combination, such as amino acids, peptones, carbohydrates, nucleotides, minerals, vitamins, etc. The medium may also contain a dye. As an indication, possible dyes may be Evans blue, neutral red, sheep blood, horse blood, an opacifier such as titanium oxide, nitroaniline, malachite green, brilliant green, one or more metabolic indicators, one or more metabolic regulators, etc.

The reaction medium may be a revealing medium or a culturing and revealing medium. In the first case, the culturing of the microorganisms is performed before seeding and, in the second case, the detection and/or identification medium also constitutes the culture medium.

The person skilled in the art may also use a bi-plate, which makes it possible to easily compare two media, comprising different substrates or different selective mixtures, onto which the same biological sample will have been deposited.

The reaction medium may comprise one or more selective agents. Selective agent is understood to be any compound capable of preventing or slowing the growth of a microorganism other than the target microorganism. Without being limiting, a concentration of between 0.01 mg/l and 5 g/l is particularly suitable for the present invention.

As a selective agent, mention can be made of antibiotics, antifungals, bile salts, crystal violet, basic fuchsine, brilliant green, etc. Antibiotics are to be understood to be any compound capable of preventing or slowing the growth of a bacterium. In particular, they belong to the beta-lactams, glycopeptides, aminosides, polypeptides, sulfamides and quinolones groups. As an indication, it is in particular possible to mention the antibiotics cloxacillin, cefotaxime, cefsulodin, ceftazidime, cefoxitin, to ceftriaxone, cefpodoxime, aztreonam, vancomycin, gentamicin, Trimethoprim, tobramycin, moxalactam, fosfomycin, D-cycloserine, Polymyxin, Colistin, and quinolones such as nalidixic acid.

Antifungals are to be understood to be any compound capable of preventing or slowing the growth of a yeast or a mould. By way of indication, it is possible to mention in particular amphotericin B, fluconazole, itraconazole, voriconazole and cycloheximide.

Cloxacillin corresponds to an antibiotic in the penicillin class. It is used in vitro to inhibit certain beta-lactamases (Giske et al., 2010; Clin. Microbiol. Infect.; 17 (4): 552-6). Dicloxacillin and flucloxacillin are advantageously considered as equivalent to cloxacillin. Preferably, cloxacillin is used at a concentration of between 25 and 300 mg/l.

PABN or PAbetaN corresponds to phenylalanine-arginine-beta-naphthylamide. This compound is known as an efflux pump inhibitor, making it possible, for example, to reduce the minimum inhibitory concentration (MIC) of chloramphenicol for strains of *Enterobacter aerogenes* (Mallea et al., 2002; Biochemical and Biophysical Research Communications 293: 1370-3). Preferably, PAbetaN is used at a concentration of between 1 and 50 mg/l.

Chromogenic substrate is to be understood to be a substrate making it possible to detect an enzymatic or metabolic activity of the target microorganisms by means of a directly or indirectly detectable signal. For direct detection, this substrate can be linked to a part acting as a fluorescent or coloured label (Orenga et al., 2009; J. Microbiol. Methods; 79(2):139-55). For indirect detection, the reaction medium according to the invention can also contain a pH indicator which is sensitive to the pH variation induced by the consumption of the substrate and which reveals the metabolism of the target microorganisms. Said pH indicator can be a chromophore or a fluorophore. As examples of chromophores, mention can be made of bromocresol purple, bromothymol blue, neutral red, aniline blue and bromocresol blue. Fluorophores include for example 4-methylumbelliferone, hydroxycoumarin derivatives or resorufin derivatives.

According to the present invention, the chromogenic substrate is preferably chosen from Indoxyl-based substrates (3-Indoxyl, 5-Bromo-3-indoxyl, 5-Iodo-3-indoxyl, 4-Chloro-3-indoxyl, 5-Bromo-4-chloro-3-indoxyl, 5-Bromo-6-chloro-3-indoxyl, 6-Bromo-3-indoxyl, 6-Chloro-3-indoxyl, 6-Fluoro-3-indoxyl, 5-Bromo-4-chloro-N-methyl-3-indoxyl, N-Methyl-3-indoxyl, Aldol™, etc.); umbelliferone-based substrates (4-Methylumbelliferone, Cyclohexenoesculetin, etc.); Alizarin-based substrates; p-Naphtholbenzein-based substrates; Nitrophenol-based substrates (ortho-Nitrophenol, para-Nitrophenol, etc.); Hydroxyquinoline-based substrates; Cathecol-based substrates (Cathecol, Dihydroxyflavone, Hydroxyflavone, etc.); Resorufin-based substrates; Chlorophenol Red-based substrates; Fluorescein-based substrates; Aminophenol-based substrates (para-Aminophenol, Dichloro-aminophenol, etc.); Naphthol-based substrates (alpha-Naphthol, 2-Naphthol, Naphthol-ASBI, etc.); Aminocoumarin-based substrates (7-Amino-4-methyl-coumarin, etc.); Naphthylamide-based substrates; Acridine-based substrates (Amino-phenyl-acridine, etc.); Amino-phenoxazine-based substrates (Amino-benzophenoxazinone, Amino-pentyl-resorufin, etc.).

As an indication, the enzymatic activities targeted by the chromogenic substrates can belong to the hydrolases group, and preferably to the osidases, esterases or peptidases groups.

As an indication, the substrates used for the detection of a beta-glucuronidase activity can in particular be 4-Methylumbelliferyl-beta-glucuronide, 5-Bromo-4-chloro-3-indolyl-beta-glucuronide, 5-Bromo-6-chloro-3-indolyl-beta-glucuronide, 6-Chloro-3-indolyl-beta-glucuronide, Alizarin-beta-glucuronide, Cyclohexenoesculetin-beta-glucuronide or salts thereof.

The substrates used for the detection of a beta-galactosidase activity can in particular be 4-Methylumbelliferyl-beta-galactoside, 5-Bromo-4-chloro-3-indolyl-beta-galactoside, 5-Bromo-6-chloro-3-indolyl-beta-galactoside, 6-Chloro-3-indolyl-beta-galactoside, Alizarin-beta-galactoside, Cyclohexenoesculetin-beta-galactoside or their salts.

The substrates used for the detection of a beta-glucosidase activity can in particular be 4-Methylumbelliferyl-beta-glucoside, 5-Bromo-4-chloro-3-indolyl-beta-glucoside, 5-Bromo-4-chloro-3-indolyl-N-methyl-beta-glucoside, 5-Bromo-6-chloro-3-indolyl-beta-glucoside, 6-Chloro-3-indolyl-beta-glucoside, Alizarin-beta-glucoside, Cyclohexenoesculetin-beta-glucoside, Nitrophenyl-beta-glucoside, Dichloroaminophenyl glucoside or their salts.

As an indication, the substrates used to detect an esterase activity can in particular be the esters of saturated or unsaturated linear fatty acids, having between 6 and 14 carbons, preferably between 7 and 9 carbons and of 4-Methylumbelliferone, 5-Bromo-4-chloro-3-indoxyl, 5-Bromo-6-chloro-3-indoxyl, 6-Chloro-3-indoxyl, 5-Bromo-3-indolyl or of Alizarin or their salts. Preferably, they are chosen from 4-Methylumbelliferyl-octanoate, 5-Bromo-4-chloro-3-indoxyl-octanoate, 5-Bromo-6-chloro-3-indoxyl-octanoate, 6-Chloro-3-indoxyl-octanoate, 5-Bromo-3-indolyl-octanoate or Alizarin-octanoate.

The substrates used for the detection of a deaminase activity can in particular be L-Tryptophan, L-Phenylalanine, L-Tyrosine and L-Histidine.

The substrates used for the detection of a sulfatase activity can in particular be 4-Methylumbelliferyl-sulfate, 5-Bromo-4-chloro-3-indoxyl-sulfate, 5-Bromo-6-chloro-3-indoxyl-sulfate, 3-indoxyl-sulfate, phenolphthalein-disulfate or their salts.

Preferably, the chromogenic substrate is chosen from: 5-Bromo-4-chloro-3-indoxyl-beta-D-glucopyranoside (X-glucoside), 5-Bromo-6-chloro-3-indoxyl-beta-D-galactopyranoside (Magenta beta-Gal), 6-Chloro-3-indoxyl-beta-D-glucuronide (Rose beta Gur), 5-Bromo-4-chloro-3-indoxyl-N-methyl-beta-D-glucopyranoside (Green A beta Glu), Methyl-beta-D-glucopyranoside (methyl beta D glucoside) and L-Tryptophan.

Incubate is to be understood to mean raising to and holding at, for between 1 and 48 hours, preferably between 4 and 24 hours, more preferably between 16 and 24 hours, an appropriate temperature, generally of between 20 and 50° C., preferably between 30 and 40° C.

Detect is to be understood to mean discerning, with the naked eye or using an optical apparatus, the existence of a growth of the target bacteria. Advantageously, when the medium employed contains a chromogenic substrate, the detection can also make it possible to identify the target bacteria. The detection takes place using an optical apparatus for the fluorescent substrates, or with the naked eye or using an optical apparatus for the coloured substrates.

Enzymatic resistance to carbapenems is to be understood to mean, as indicated supra, the resistance to carbapenem antibiotics due to the expression, by the target bacteria, of carbapenemases.

The most frequently encountered bacteria which are resistant to carbapenems are, as indicated supra: *Escherichia coli, Enterobacter cloacae, Enterobacter aerogenes, Citrobacter* sp., *Klebsiella pneumoniae, Klebsiella oxytoca, Pseudomonas aeruginosa, Providencia rettgeri, Pseudomonas putida, Stenotrophomonas maltophilia, Acinetobacter baumanii, Comamonas* sp., *Aeromonas* sp., *Morganella morganii, Enterococcus* sp., *Proteus mirabilis, Salmonella senftenberg, Serratia marcescens, Salmonella typhimurium*, etc.

The present invention also relates to a culture medium for detecting and/or identifying bacteria exhibiting a resistance to carbapenems, said culture medium corresponding to a basic culture medium, further comprising at least one chromogenic substrate and at least faropenem and/or doripenem.

The examples developed below aim to facilitate the understanding of the invention. They are given by way of explanation and are not intended to limit the scope of the invention.

EXAMPLES

Example 1

Test of Faropenem on Pure Strains

1. Media and Microorganisms

Seventy-nine strains of Gram-negative bacteria, of which 69 are enterobacteria and 10 non-enterobacteria (non-fermenting bacteria), whose resistance characteristics are set out in Table I, were tested on media containing different concentrations of faropenem in order to establish the sensitivity/specificity of each formulation. The dishes were read after 24 hours of incubation at 37° C.

TABLE I

| resistance mechanisms characterising the strains tested | |
|---|---|
| | Number of strains |
| ESBL or cephalosporinase (ESBL or Case) | 15 |
| Class A KPC carbapenemase (KPC) | 34 |
| Class A non-KPC carbapenemase (Carba A) | 8 |
| Class B carbapenemase (Carba B) | 10 |
| Class D carbapenemase (Oxa) | 6 |
| Impermeability resistance (IR) | 6 |

The medium used is a conventional agar medium comprising at least one chromogenic substrate, and supplemented with faropenem at the following concentrations:

| | Medium 1 | Medium 2 | Medium 3 | Medium 4 | Medium 5 | Medium 6 | Medium 7 | Medium 8 |
|---|---|---|---|---|---|---|---|---|
| Faropenem (mg/L) | 0 | 0.5 | 1 | 2 | 4 | 8 | 16 | 32 |

2. Test

The media are divided into 120×120 square dishes.

The seeding is performed from 24-h pre-cultures at 37° C. on trypcase soy agar.

For each strain, a 0.5 McF suspension in physiological water is produced and then diluted 1/100.

Each suspension is spot-seeded (1 to 2 µL) on each medium with the aid of a multi-point inoculator according to the Agar Dilution (AD) method.

Readings are performed after 24 hours of incubation at 37° C.

For interpretation, the following cases are considered as corresponding to growth inhibition:
absence of bacterial growth
number of colonies≤3

The presence of 4 colonies or more is considered to be positive growth.

3. Results and Interpretation

Detection sensitivity and specificity are indicated in Table II.

Table II: detection sensitivity/specificity of the carbapenemase-producing strains on a medium containing 16 mg/L of faropenem.

TABLE II

| detection sensitivity/specificity of the carbapenemase-producing strains on a medium containing 16 mg/L of faropenem. | | |
|---|---|---|
| | Inoculum: 0.5 McF | Inoculum: 0.5 McF diluted 1/100 |
| Detection sensitivity | 53/58 | 53/58 |
| | 91.4% | 91.4% |
| Detection specificity | 14/21 | 15/21 |
| | 66.7% | 71.4% |

Faropenem, used for example at 16 mg/L, makes it possible to clearly distinguish between the carbapenemase-producing bacteria and the other types of resistance. The MIC of the totality of KPC strains is always >32, whatever the inoculum tested. All of the KPC strains develop on the medium comprising faropenem at 16 mg/L.

Example 2

Doripenem Test on Pure Strains
1. Media and Microorganisms

One hundred strains of Gram-negative bacteria, of which 98 are enterobacteria and 2 non-enterobacteria (non-fermenting bacteria), whose resistance characteristics are set out in Table III, were tested on media containing different concentrations of faropenem in order to establish the sensitivity and the specificity of each formulation. A medium containing 0.125 mg/L meropenem was also tested. The chromogenic medium UriSelect® (Biorad) is used as a growth control. The dishes were read after 24 h and 48 h of incubation at 37° C.

TABLE III resistance mechanisms characterising the strains tested

|  | Number of strains |
|---|---|
| ESBL | 42 |
| Cephalosporinase: AmpC (30), others (4) | 34 |
| Class A KPC carbapenemase (KPC) | 5 |
| Class B carbapenemase (Carba B) | 19 |

The medium used is a conventional agar medium comprising at least one chromogenic substrate, and supplemented with carbapenem at the following concentrations:

|  | Medium A | Medium B | Medium C | Medium D | Medium E |
|---|---|---|---|---|---|
| Doripenem (mg/L) | 0 | 0.065 | 0.125 | 0.25 | 0 |
| Meropenem (mg/L) | 0 | 0 | 0 | 0 | 0.125 |

2. Test

The media are divided into 90 mm dishes.

Each strain is spot-seeded on each medium, using 1 μL (containing around $10^4$ microorganisms) of a diluted 0.5 McF suspension.

Readings are performed after 24 and 48 hours of incubation at 37° C.

3. Results and Interpretation

The results are brought together in Table IV.

TABLE IV percentage of strains of each resistance category which develop on the different media.

|  | Uriselect ® (Biorad) | Medium A | Medium B 0.065 mg/L doripenem | Medium C 0.125 mg/L doripenem | Medium D 0.25 mg/L doripenem | Medium E 0.125 mg/L meropenem (mg/l) |
|---|---|---|---|---|---|---|
| Carbapenemases | 100 | 100 | 83 | 50 | 33 | 50 |
| Others | 100 | 98.7 | 8 | 5 | 4 | 5 |

Example 3

Comparison of the Medium Containing Doripenem with a Commercially Available Medium
1. Media and Microorganisms One hundred enterobacteria strains, of which 25 produce carbapenemases and of which the resistance characteristics are set out in Table V, were tested on medium B described supra (0.065 mg/L of doripenem) and on the COLOREX™ KPC medium. This latter medium is provided by BioMed Diagnostics Inc. and corresponds to the CHROMagar™ KPC ready-to-use medium.

TABLE V resistance mechanisms characterising the strains tested

|  | Number of strains |
|---|---|
| ESBL | 42 |
| Cephalosporinase AmpC (29), others (4) | 33 |
| Class A KPC carbapenemase | 6 |
| Class B carbapenemase (Carba B) | 19 |

2. Test

Each strain is spot-seeded on each medium, using 1 μL (containing around $10^4$ microorganisms) of a diluted 0.5 McF suspension.

Readings are performed after 24 and 48 hours of incubation at 37° C.

3. Results and Interpretation

TABLE VI percentage of strains which develop on the media

|  | COLOREX KPC 24 h | COLOREX KPC 48 h | Medium B (0.065 mg/L doripenem) 24 h | Medium B (0.065 mg/L doripenem) 48 h |
|---|---|---|---|---|
| % carbapenemase-producing strains | 80 | 80 | 88 | 92 |
| % other strains | 5 | 5 | 10.7 | 10.7 |

The medium containing 0.065 mg/L of doripenem permits the growth of 92% of the carbapenemase-producing Enterobacteria tested, against only 80% on the commercial medium, whatever the incubation time. The medium containing doripenem is therefore superior to the commercial medium.

Example 4

Tests on Clinical Specimens
1. Media and Specimens

Two hundred swabs (with transport medium) loaded with bacterial populations isolated from stools were seeded on medium B indicated supra (0.065 mg/L of doripenem), on a medium similar to medium 7 indicated supra (16 mg/L of faropenem) and on the COLOREX™ KPC medium.

2. Test 0.5 mL of sterile water are added to the tubes containing the swab and the transport medium. The tubes are vortexed.

10 μl of the obtained suspension are seeded in 4 quadrants on each medium. Readings of the media are performed after 24 hours of incubation at 37° C.

3. Results and Interpretation

TABLE VII results from screening carbapenemase-producing strains from bacterial populations isolated from stools.

|  | All media mixed | Medium B (0.065 mg/L doripenem) | Colorex KPC | Medium 7 (16 mg/L faropenem) |
|---|---|---|---|---|
| No growth |  | 141 | 156 | 145 |
| Positive Specimens |  |  |  |  |
| Metallo-carbapenemase |  |  |  |  |
| E. coli | 30 | 30 | 12 | 30 |
| E. cloacae | 22 | 22 | 22 | 17 |
| Citrobacter sp. | 7 | 3 | 2 | 6 |
| K. pneumoniae | 3 | 0 | 2 | 2 |
| P. rettgeri | 2 | 0 | 2 | 0 |
| Total CPE[1]: | 64 | 55 | 40 | 55 |
| Sensitivity (%) |  | 85.9 | 62.5 | 85.9 |
| S. maltophilia | 4 | 4 | 3 | 4 |
| A. baumannii | 3 | 2 | 3 | 0 |
| Ps putida | 1 | 0 | 1 | 0 |
| Comamonas aquatic | 1 | 0 | 1 | 0 |
| Aeromonas sp. | 1 | 0 | 1 | 0 |
| Negative Specimens |  |  |  |  |
| Metallo-carbapenemase |  |  |  |  |
| E. coli | 13 | 13 | 2 | 9 |
| A. baumannii | 4 | 3 | 3 | 1 |
| P. aeruginosa | 1 | 1 | 1 | 0 |
| M. morganii | 5 | 5 | 1 | 1 |
| Total false positives: | 33 | 28 | 16 | 15 |
| (Only Gram-negatives) |  |  |  |  |
| Enterococcus sp. | 13 | 11 | 0 | 13 |

[1]Carbapenemase-producing enterobacteria

The 64 strains of Carbapenemase-producing Enterobacteria (CPE), of the NDM-1 type, were isolated from 37 stool specimens. Medium 7 comprising 16 mg/L of faropenem exhibits the best performances in terms of sensitivity (86%) and specificity (15 Gram-false positives). Medium B comprising 0.065 mg/L of doripenem exhibits an equally high sensitivity, but a slightly lower specificity (28 Gram-false positives). The COLOREX™ KPC medium makes it possible to detect only 62.5% of the CPE, for a specificity/selectivity equivalent to that of the medium containing faropenem.

In conclusion, the method according to the invention of detecting carbapenem-resistant bacteria, demonstrates through examples 1, 2, 3 and 4, the improvement which it brings to the state of the art, both on laboratory strains and on clinical specimens.

Example 5

Test of Stability of the Different Carbapenems in Agar Medium

Agar media modelled on those indicated supra were prepared and kept at a temperature of between 2 and 8° C. for up to 9 weeks (63 days).

ESBL and AmpC strains, and carbapenemases from class B, IR or KPC, were seeded on these different media on D0, D14, D42 and D63.

These tests have made it possible to show that doripenem and faropenem exhibit a stability in agar medium which is close to that of ertapenem, and greater than that of imipenem and of meropenem.

Example 6

Impact of cloxacillin and/or PAbetaN on the Minimum Inhibitory Concentrations (MICs) of the strains which are impermeability-resistant (IR) or exhibit another non-enzymatic resistance mechanism, or are carbapenemase-producing, in the presence of faropenem.

1. Media and Microorganisms

Seventy-seven strains of Gram-negative bacteria, of which 71 are enterobacteria and 6 non-enterobacteria (non-fermenting bacteria), whose resistance characteristics are set out in Table VIII, were tested on media containing different concentrations of faropenem and cloxacillin, with or without PAbetaN, in order to establish the sensitivity and the specificity of each formulation. The tested media are described in Table IX.

TABLE VIII mechanisms of resistance to antibiotics characterising the strains tested.

|  | Number of strains |
|---|---|
| ESBL (7), Cephalosporinase AmpC (9) | 16 |
| Class A KPC carbapenemase (KPC) | 10 |
| Class A non-KPC carbapenemase (Class A) | 5 |
| Class B NDM-1 carbapenemase (NDM) | 15 |
| Class B non-NDM carbapenemase (Class B) | 6 |
| Class D OXA carbapenemase (OXA) | 6 |
| Impermeability resistance (IR) | 19 |

TABLE IX composition of the tested media

| Media | C | 1 | 5 | 9 | 2 | 6 | 10 | 3 | 7 | 11 | 4 | 8 | 12 | 13 | 16 | 19 | 14 | 17 | 20 | 15 | 18 | 21 |
|---|---|---|---|---|---|---|---|---|---|---|---|---|---|---|---|---|---|---|---|---|---|---|
| Chromogenic base |  |  |  |  |  |  |  |  |  |  | 47 g/L |  |  |  |  |  |  |  |  |  |  |  |
| PABN (mg/L) |  |  |  |  |  | 0 |  |  |  |  |  |  |  |  |  |  | 25 |  |  |  |  |  |
| Cloxacillin (mg/L) |  |  | 0 |  |  | 50 |  |  | 100 |  |  | 200 |  |  | 50 |  |  | 100 |  |  | 200 |  |
| Faropenem (mg/L) | 0 | 8 | 16 | 32 | 8 | 16 | 32 | 8 | 16 | 32 | 8 | 16 | 32 | 8 | 16 | 32 | 8 | 16 | 32 | 8 | 16 | 32 |

2. Test

The chromogenic media are divided into 120×120 square dishes.

The seeding is performed from 24-h pre-cultures at 37° C. on trypcase soy agar. For each strain, a 0.5 McF suspension in physiological water is produced. Each suspension is spot-seeded (1 to 2 μL) on each medium with the aid of a multi-point inoculator according to the Agar Dilution (AD) method. Readings are performed after 24 hours of incubation at 37° C.

3. Results

The results are brought together in Table X.

An absence of bacterial growth or a number of colonies which is less than or equal to 3 are considered as corresponding to growth inhibition. The presence of 4 colonies or more is considered to be positive growth.

These results also confirm the better inhibition of the IR strains in the presence of cloxacillin+PAbetaN. This effect is visible for the majority of the cloxacillin and faropenem concentrations tested, but is very distinctly marked in the presence of 200 mg/L of cloxacillin (whatever the faropenem concentration).

TABLE X impact of cloxacillin and/or of PAbetaN on the growth (number of strains developing) of the strains which produce carbapenemases or which are resistant to beta-lactams due to another resistance mechanism, in the presence of faropenem

| Media | C | 1 | 5 | 9 | 2 | 6 | 10 | 3 | 7 | 11 | 4 | 8 | 12 | 13 | 16 | 19 | 14 | 17 | 20 | 15 | 18 | 21 |
|---|---|---|---|---|---|---|---|---|---|---|---|---|---|---|---|---|---|---|---|---|---|---|
| PABN (mg/L) | | | | | | 0 | | | | | | | | | | | | 25 | | | | |
| Cloxacillin (mg/L) | | | 0 | | | 50 | | | 100 | | | 200 | | | 50 | | | 100 | | | 200 | |
| Faropenem (mg/L) | 0 | 8 | 16 | 32 | 8 | 16 | 32 | 8 | 16 | 32 | 8 | 16 | 32 | 8 | 16 | 32 | 8 | 16 | 32 | 8 | 16 | 32 |
| ESBL | 7 | 1 | 1 | 0 | 1 | 0 | 0 | 1 | 0 | 0 | 1 | 0 | 0 | 3 | 1 | 0 | 1 | 0 | 0 | 1 | 0 | 0 |
| AmpC | 9 | 3 | 2 | 2 | 2 | 2 | 2 | 2 | 2 | 2 | 2 | 2 | 1 | 4 | 3 | 2 | 3 | 2 | 2 | 2 | 2 | 0 |
| IR | 19 | 16 | 15 | 10 | 14 | 9 | 4 | 11 | 6 | 2 | 11 | 6 | 1 | 11 | 10 | 5 | 10 | 5 | 1 | 7 | 1 | 1 |
| Total non-carbapenemases | 35 | 20 | 18 | 12 | 17 | 11 | 6 | 14 | 8 | 4 | 14 | 8 | 2 | 18 | 14 | 7 | 14 | 7 | 3 | 10 | 3 | 1 |
| Class A | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| Class B | 6 | 4 | 3 | 3 | 4 | 3 | 3 | 3 | 3 | 3 | 3 | 3 | 5 | 3 | 2 | 4 | 2 | 2 | 4 | 2 | 2 | |
| KPC | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| NDM | 15 | 12 | 8 | 8 | 12 | 8 | 6 | 12 | 9 | 7 | 12 | 8 | 7 | 14 | 12 | 8 | 12 | 12 | 6 | 10 | 9 | 6 |
| OXA | 6 | 4 | 4 | 2 | 4 | 4 | 1 | 4 | 3 | 2 | 4 | 4 | 1 | 5 | 4 | 0 | 5 | 4 | 0 | 5 | 4 | 0 |
| Total carbapenemases | 42 | 35 | 30 | 28 | 35 | 31 | 25 | 34 | 30 | 27 | 34 | 30 | 26 | 39 | 34 | 25 | 36 | 33 | 23 | 34 | 30 | 23 |

4. Interpretation

TABLE XI sensitivity and specificity of media containing faropenem in the presence of cloxacillin, combined or not with PAbetaN, for strains which produce carbapenemases or which are resistant to beta-lactams due to another resistance mechanism.

| Media | C | 1 | 5 | 9 | 2 | 6 | 10 | 3 | 7 | 11 | 4 | 8 | 12 | 13 | eve | 19 | 14 | 17 | 20 | 15 | 18 | 21 |
|---|---|---|---|---|---|---|---|---|---|---|---|---|---|---|---|---|---|---|---|---|---|---|
| PABN (mg/L) | | | | | | 0 | | | | | | | | | | | | 25 | | | | |
| Cloxacillin (mg/L) | | | 0 | | | 50 | | | 100 | | | 200 | | | 50 | | | 100 | | | 200 | |
| Faropenem (mg/L) | 0 | 8 | 16 | 32 | 8 | 16 | 32 | 8 | 16 | 32 | 8 | 16 | 32 | 8 | 16 | 32 | 8 | 16 | 32 | 8 | 16 | 32 |
| Sensitivity (%) | 100 | 83 | 71 | 67 | 83 | 74 | 60 | 81 | 71 | 64 | 81 | 71 | 62 | 93 | 81 | 60 | 86 | 79 | 55 | 81 | 71 | 55 |
| Specificity (%) | 0 | 43 | 49 | 66 | 51 | 69 | 83 | 60 | 77 | 89 | 60 | 77 | 94 | 49 | 60 | 80 | 60 | 80 | 91 | 71 | 91 | 97 |

4a. Impact of Cloxacillin and PAbetaN on IR Strains

TABLE XII

Effects of cloxacillin, associated or not with PAbetaN, on the growth of the 19 IR strains tested.

| PAbetaN (mg/L) | | | | | | 0 | | | | | | | | | | | | 25 | | | | |
|---|---|---|---|---|---|---|---|---|---|---|---|---|---|---|---|---|---|---|---|---|---|---|
| Cloxacillin (mg/L) | | | 0 | | | 50 | | | 100 | | | 200 | | | 50 | | | 100 | | | 200 | |
| Faropenem (mg/L) | 0 | 8 | 16 | 32 | 8 | 16 | 32 | 8 | 16 | 32 | 8 | 16 | 32 | 8 | 16 | 32 | 8 | 16 | 32 | 8 | 16 | 32 |
| No. IR developing (/19) | 19 | 16 | 15 | 10 | 14 | 9 | 4 | 11 | 6 | 2 | 11 | 6 | 1 | 11 | 10 | 5 | 10 | 5 | 1 | 7 | 1 | 1 |

Faropenem alone has little impact on these strains, up to a concentration of 16 mg/L. An inhibition of the IR strains is observed from the moment when 50 mg/L of cloxacillin is added, and is even more marked for the highest concentrations of faropenem tested (16 and 32 mg/L). This inhibitory effect increases with the concentration of cloxacillin (for example, for a concentration of 16 mg/L of faropenem, the addition of 50 mg/L or 200 mg/L cloxacillin respectively permits the inhibition of 6 and 9 additional IR strains). A combined effect of the concentration of faropenem and of that of cloxacillin on the IR strains is observed.

4b. Impact of Cloxacillin and PAbetaN on the Carbapenemase-Producing Strains

The results obtained in presence of faropenem confirm that the cloxacillin alone has little or no impact on the growth of the carbapenemase-producing strains (at the 3 concentrations of faropenem tested). They also confirm that associating PAbetaN with the cloxacillin makes it possible to increase the MIC of certain strains to carbapenems so long as the faropenem concentration remains less than 32 mg/L. Thus, the detection sensitivity in the presence of 8 or 16 mg/L of faropenem associated with 50 or 100 mg/L of cloxacillin is greater in the presence of PAbetaN. For 200 mg/L of cloxacillin and 8 or 16 mg/L of faropenem, the addition of PAbetaN does not change the detection sensitivity.

5. Conclusion

These results confirm the inhibitory role of cloxacillin on the strains which are impermeability-resistant, in the presence of a carbapenem. These results also confirm optimum inhibition of the IR strains when cloxacillin is associated with PAbetaN. The addition of cloxacillin and PAbetaN thus makes it possible to very greatly increase the specificity of the medium.

The addition of cloxacillin (at the 3 concentrations tested) and of PAbetaN (25 mg/L) into the medium does not alter the detection of the carbapenemase-producing strains in the presence of 8 or 16 mg/L of faropenem. It is confirmed that the addition of PAbetaN tends to improve their detection at faropenem concentrations equal to 8 or 16 mg/L, associated with 50 or 100 mg/L cloxacillin.

In the presence of faropenem, the results observed with ertapenem (E-test) are therefore confirmed, namely a better inhibition of the IR strains by addition of cloxacillin, and an improvement of the detection of the carbapenemase-producing strains in the presence of PAbetaN.

The invention claimed is:

1. A process for detecting whether at least one carbapenem-resistant bacterial strain is present in a biological sample, comprising:
   contacting the biological sample with a culture medium to obtain an inoculated culture medium, the culture medium comprising (i) at least one chromogenic substrate, and (ii);
   incubating the inoculated culture medium to culture the carbapenem-resistant bacterial strain if present in the biological sample; and
   detecting whether the carbapenem-resistant bacterial strain is present on or in the culture medium.

2. The process of claim 1, wherein the carbapenem-resistant bacterial strain is an NDM-1 bacterial strain.

3. The process of claim 1, wherein the culture medium comprises faropenem at a concentration from 2 to 32 mg/L.

4. The process of claim 3, wherein the culture medium further comprises doripenem at a concentration from 0.05 to 2 mg/L.

5. The process of claim 1, wherein the chromogenic substrate detects glucuronidase, glucosidase, galactosidase, esterase, sulfatase, or deaminase activity.

6. The process of claim 1, wherein the chromogenic substrate is selected from the group consisting of 5 Bromo-4 chloro-3 indoxyl-beta D glucopyranoside (X-glucoside), 5 Bromo-6 chloro-3 indoxyl-beta D galactopyranoside (Magenta beta-Gal), 6 Chloro-3 indoxyl-beta D glucuronide (Rose beta Gur), 5 Bromo-4 chloro-3 indoxyl-N methyl-beta D glucopyranoside (Green A beta Glu), and L Tryptophan.

7. The process of claim 1, wherein the culture medium is a solid culture medium.

8. The process of claim 1, wherein the culture medium is a liquid culture medium.

9. The process of claim 1, wherein the culture medium further comprises cloxacillin, dicloxacillin, or flucloxacillin.

10. The process of claim 3, wherein the culture medium further comprises cloxacillin at a concentration from 25 to 300 mg/L.

11. The process of claim 1, wherein the culture medium further comprises cloxacillin and phenylalanine-arginine-beta-naphthylamide (PAbetaN).

12. The process of claim 3, wherein the culture medium further comprises cloxacillin at a concentration from 25 to 300 mg/L, and phenylalanine-arginine-beta-naphthylamide (PAbetaN) at a concentration from 1 to 50 mg/L.

13. The process of claim 1, wherein the culture medium comprises faropenem at a concentration from 8 to 32 mg/L.

14. The process of claim 3, wherein the culture medium further comprises doripenem at a concentration from 0.065 to 0.25 mg/L.

15. The process of claim 1, wherein the culture medium further comprises doripenem.

16. A process for detecting whether at least one carbapenem-resistant bacterial strain is present in a biological sample, comprising:
   contacting the biological sample with a culture medium to obtain an inoculated culture medium, the culture medium comprising (i) at least one chromogenic substrate, (ii) at least one of faropenem or doripenem, (iii) at least one of cloxacillin, dicloxacillin, or flucloxacillin, and (iv) phenylalanine-arginine-beta-naphthylamide (PAbetaN);
   incubating the inoculated culture medium to culture the carbapenem-resistant bacterial strain if present in the biological sample; and
   detecting whether the carbapenem-resistant bacterial strain is present on or in the culture medium.

17. The process of claim 16, wherein the culture medium comprises cloxacillin.

18. The process of claim 16, wherein the culture medium comprises at least one of faropenem or doripenem at a concentration from 0.05 to 32 mg/L.

19. The process of claim 18, wherein the culture medium comprises cloxacillin at a concentration from 25 to 300 mg/L, and PAbetaN at a concentration from 1 to 50 mg/L.

20. The process of claim 16, wherein the culture medium comprises faropenem at a concentration from 2 to 32 mg/L.

21. The process of claim 16, wherein the culture medium comprises doripenem at a concentration from 0.05 to 2 mg/L.

* * * * *